United States Patent [19]

Flowers

[11] Patent Number: 4,593,692

[45] Date of Patent: Jun. 10, 1986

[54] PLETHYSMOGRAPH CUFF BLADDER

[75] Inventor: Edward P. Flowers, Mountain View, Calif.

[73] Assignee: Medasonics, Inc., Mountain View, Calif.

[21] Appl. No.: 617,232

[22] Filed: Jun. 4, 1984

[51] Int. Cl.⁴ .................. A61B 17/12; A61B 5/02; A61M 29/02

[52] U.S. Cl. .................. 128/327; 128/686; 128/344; 604/99; 604/118; 604/98

[58] Field of Search .................. 128/686, 327, 344; 604/99, 118, 96, 97, 98, 100, 101, 102, 103

[56] References Cited

U.S. PATENT DOCUMENTS

| | | | |
|---|---|---|---|
| 2,068,173 | 1/1937 | Galves | 128/327 |
| 2,981,251 | 4/1961 | Berman | 128/686 |
| 3,756,239 | 9/1973 | Smythe | 128/327 |
| 3,760,795 | 9/1973 | Adelhed | 128/686 |
| 3,906,937 | 9/1975 | Aronson | 128/327 |
| 3,939,820 | 2/1976 | Grayzel | 128/344 |
| 4,346,698 | 8/1982 | Hansen et al. | 604/98 |

FOREIGN PATENT DOCUMENTS

| | | | |
|---|---|---|---|
| 655385 | 4/1979 | U.S.S.R. | 128/686 |

*Primary Examiner*—Andrew H. Metz
*Assistant Examiner*—Chung K. Pak
*Attorney, Agent, or Firm*—Fliesler, Dubb, Meyer & Lovejoy

[57] ABSTRACT

An inflatable plethysmographic cuff bladder comprising interior members for preventing the trapping of an inflating medium in the bladder when the inflating medium is rapidly evacuated therefrom. The interior members comprise members which project inwardly from facing interior walls of the bladder and members which are inserted in the bladder and extend outwardly toward the facing interior walls of the bladder. In all cases, the members cooperate to form channels assisting the flow of inflating medium from the bladder when the bladder is rapidly evacuated of the inflating medium.

9 Claims, 8 Drawing Figures

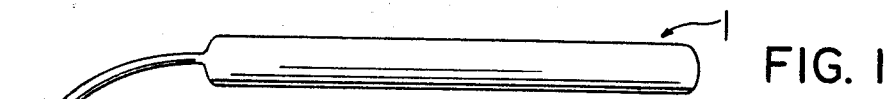
FIG. 1
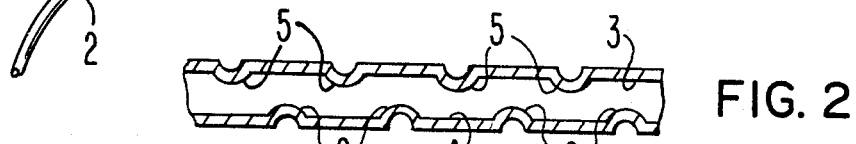
FIG. 2
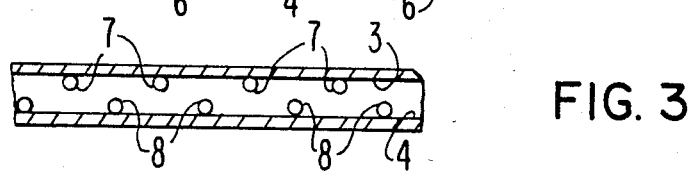
FIG. 3
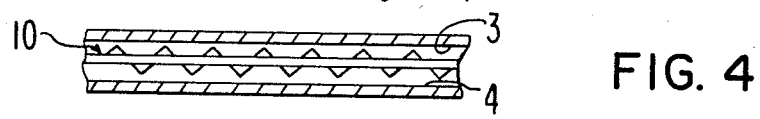
FIG. 4
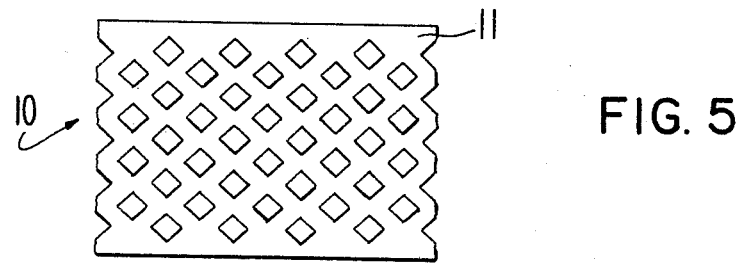
FIG. 5
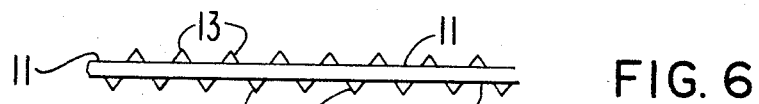
FIG. 6
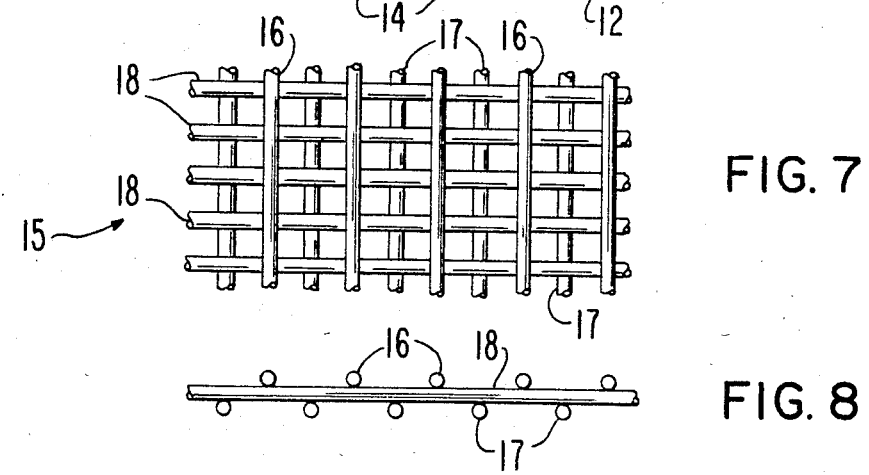
FIG. 7
FIG. 8

PLETHYSMOGRAPH CUFF BLADDER

FIELD OF THE INVENTION

The present invention refers in general to plethysmograph inflatable cuff bladders and in particular to a plethysmograph inflatable cuff bladder comprising means for promoting rapid evacuation of the bladder.

BACKGROUND OF THE INVENTION

Plethysmographic apparatus is used for measuring changes in blood volume or flow in an appendage, e.g. arm, leg, etc. In practice, the apparatus comprises a device which is used to artificially occlude one or more blood vessels in the appendage. After the vessels are occluded to their maximum distension, the device effecting the artificial occlusion is rapidly removed and a strain gauge or other apparatus is used to measure the rate at which the artificially occluded vessels return to their former nonartificially occluded state. The rate at which the occluded vessels return to their nonartificially occluded state is a measure of their physical condition and consequently, a measure of the extent of any existing disease or obstruction to which the vessels have been or are being subjected.

In most plethysmographic apparatus, the device used for occluding one or more blood vessels in an appendage is an inflatable cuff bladder contained in a cuff which encircles the appendage. The bladder is inflated with an inflating medium, usually air, until the desired vessels are occluded. After the desired vessels are occluded, the inflating medium is rapidly removed from the bladder and the necessary measurements are made.

In one method used to evacuate the bladder of the inflating medium, a valve, or the like, in a hose or other apparatus used for inflating the bladder is opened to the atmosphere for discharging the inflating medium to the atmosphere. In cases involving severely diseased blood vessels, it is found that the rate of return of the blood vessels to their nonartificially occluded state is low enough that the time it takes to evacuate the bladder and remove the occlusion by simply venting the bladder to the atmosphere is sufficient. However, this is found not to be true in cases involving healthy blood vessels or less severely diseased blood vessels. In those cases, the bladder must be evacuated more rapidly or the occluding effects of the partially evacuated bladder will adversely affect the measurements made.

To evacuate the bladder more rapidly in cases involving healthy or less severely diseased blood vessels, it has become the practice to connect the bladder suddenly to a vacuum, or other low pressure, chamber. With the bladder connected to a vacuum chamber, it has been found that the bladder can be, at least partially, rapidly evacuated at a rate which exceeds the the rate of return of healthy blood vessels to their nonartificially occluded state. A system of the type in which a bladder is evacuated using a vacuum chamber is disclosed in U.S. Pat. No. 4,205,688, granted June 3, 1980.

While the rapid evacuation of a bladder using a vacuum chamber, or the like, has improved plethysmographic measurements to some extent, it has been found that often the bladder collapses near the point of evacuation hose attachment thereto with the result that some of the inflating medium becomes trapped in the bladder thus slowing the release of the constricting effect of the bladder on the appendage.

SUMMARY OF THE INVENTION

In view of the foregoing, a principle object of the present invention is a plethysmographic bladder which includes means for preventing the trapping of an inflating medium therein when the bladder is rapidly evacuated of the inflating medium.

As mentioned above, it has been found that a certain amount of the inflating medium used for inflating a plethysmographic bladder is trapped in the bladder when the bladder is rapidly evacuated. The trapping of the inflating medium in the bladder is found to be, at least partly, caused by collapsing of the bladder near the point of attachment of the evacuating hose thereto to such an extent that extensive portions of facing interior walls in the bladder come into contact with each other and restrict the flow of the inflating medium to the evacuation hose outlet.

To prevent the above described facing interior wall contact when a plethysmographic bladder is rapidly evacuated, there is provided, in one embodiment of the present invention, a plethysmographic bladder comprising interior wall surfaces which are dimpled or embossed so to as to provide staggered inwardly directed wall portions. In another embodiment of the invention there is provided on the interior walls of a plethysmographic bladder, a plurality of staggered inwardly directed beads or pegshaped members.

In still another embodiment of the invention there is provided between the interior walls of a plethysmographic bladder, a porous mesh material, such as a screen-like material, or entwined coil-like material, such as coarse steel wool, or the like.

In all of the embodiments, the means used for preventing the trapping of the inflating medium in the bladder forms non-collapsible channels for the flow of the medium to the evacuating hose outlet even when very rapid bladder evacuation techniques are used.

BRIEF DESCRIPTION OF THE DRAWING

The above and other objects, features and advantages of the present invention will become apparent from the following detailed description of the accompanying drawing in which:

FIG. 1 is side view of a plethysmographic bladder according to the present invention.

FIG. 2 is a partial cross-sectional view of one embodiment of the present invention.

FIG. 3 is a partial cross-sectional view of another embodiment of the present invention.

FIG. 4 is a partial cross-sectional view of still another embodiment of the present invention.

FIG. 5 is a partial plan view of a screen member, such as used in the embodiment of FIG. 4.

FIG. 6 is a side view of FIG. 5.

FIG. 7 is a partial plan view of another screen member used in still another embodiment of the present invention.

FIG. 8 is a side view of FIG. 7.

DETAILED DESCRIPTION OF THE DRAWING

Referring to FIG. 1, there is provided in accordance with the present invention, a plethysmographic bladder designated as 1. The bladder 1 is typically made of rubber, a flexible plastic or other suitable material. Coupled to one end of the bladder 1, there is provided a noncollapsible hose 2.

In use, in a typical plethysmographic system, the hose 2 is coupled to a source of an inflating medium, such as air, for inflating the bladder 1. Thereafter, it is selectively and sudddenly coupled to a vacuum chamber, or the like (not shown), for rapidly evacuating the bladder 1.

Referring to FIG. 2, in one embodiment of the present invention, the bladder 1 is provided with facing interior walls 3,4. The walls 3,4 are dimpled or embossed in any suitable manner so as to provide a plurality of inwardly projecting, staggered, raised, channel-shaped portions or reliefs 5,6, respectively.

Referring to FIG. 3, in another embodiment of the present invention, there is provided on the interior walls 3 and 4, in place of the reliefs 5,6, a plurality of inwardly projecting, staggered bead-like or peg-like members 7,8, respectively.

Referring to FIGS. 4, 5 and 6, in another embodiment of the present invention, there is provided between the interior walls 3 and 4, in place of the inwardly projecting members of FIGS. 2,3, an embossed member 10 comprising a pair of opposite surfaces 11,12 from which there extends outwardly a plurality of diamond-shaped reliefs 13,14, respectively.

In use, the member 10 is sized to fit within the interior of the bladder 1 and extends from one to the other end thereof.

Referring to FIGS. 7 and 8, there is provided in another embodiment of the present invention a screen-shaped member 15. Member 15 comprises a sandwich of a plurality of sets 16, 17 and 18 of elongated wire-like members, which extend over one another with the wire-like members in sets 16 and 17 creating surfaces which extend outwardly from the surfaces of the wire-like members in set 18.

In practice, the member 15 may be molded of a plastic or other suitable material. It is also possible to use the member 15 with only two of the three sets of wire-like members and to arrange the wire-like members of one set to extend at an angle across the wire-like members of the other set. A plastic screen-like material of the type just described, also known as a vinyl mesh material, is sold by ADPI Enterprises of Chicago, Ill. As in the case of the embodiments of FIGS. 5 and 6, in use, the member 15 is sized to fit within the interior of the bladder 1.

In the embodiments described, the inwardly projecting members of the embodiments of FIGS. 2 and 3 and the outwardly projecting members of the embodiments of FIGS. 5–8 cooperate to prevent the interior walls 3,4 of the bladder 1 from contacting, and to form channels for the evacuation of the inflating medium from the bladder 1 when the bladder 1 is rapidly evacuated of the inflating medium.

While a preferred and several alternative embodiments of the present invention are described above, it is contemplated that various modifications may be made thereto without departing from the spirit and scope of the present invention. Accordingly, it is intended that the scope of the invention not be limited to the above described embodiments, but rather, be determined by reference to the claims hereinafter provided.

What is claimed is:

1. An inflatable cuff bladder comprising:
   a chamber having facing interior walls which is adapted to be inflated with an inflating medium and thereafter evacuated of said medium; and
   means located in the interior of said chamber, said means extending from one to the other end thereof between said facing walls, for preventing the collapsing together of said facing walls and the trapping of said inflating medium in said chamber when said chamber is suddenly evacuated of said inflating medium.

2. An inflatable cuff bladder according to claim 1 wherein said preventing means which extends from one to the other end of said chamber between said facing walls comprises a porous medium.

3. An inflatable cuff bladder according to claim 2 wherein said porous medium comprises a porous mesh material.

4. An inflatable cuff bladder according to claim 2 wherein said porous medium comprises a coiled material.

5. An inflatable cuff bladder according to claim 2 wherein said porous medium comprises a screen-like material.

6. In an inflatable cuff bladder including a chamber having facing interior walls which is adapted to be inflated with an inflating medium and thereafter evacuated of said medium, the improvement comprising:
   a plurality of members which project inwardly from each of said facing interior walls, said members on one of said walls being staggered relative to said members on the other of said walls, for preventing said facing interior walls from making inflating medium trapping contact with each other when said chamber is suddenly evacuated of said inflating medium.

7. An inflatable cuff bladder according to claim 6 wherein said members comprise channel forming members.

8. An inflatable cuff bladder according to claim 6 wherein said members comprise bead-shaped members.

9. An inflatable cuff bladder according to claim 6 wherein said members comprise peg-shaped members.

* * * * *